United States Patent [19]

Hatahira

[11] Patent Number: 4,503,157
[45] Date of Patent: Mar. 5, 1985

[54] SINTERED APATITE BODIES AND COMPOSITES THEREOF

[75] Inventor: Seiichi Hatahira, Handa, Japan

[73] Assignee: Ina Seito Co., Ltd., Tokoname, Japan

[21] Appl. No.: 489,520

[22] Filed: Apr. 28, 1983

[30] Foreign Application Priority Data

Sep. 25, 1982 [JP] Japan .................................. 57-167013
Oct. 30, 1982 [JP] Japan .................................. 57-191347

[51] Int. Cl.$^3$ ............................................. C04B 35/00
[52] U.S. Cl. ............................................. 501/1; 3/1.9; 106/35; 264/60; 264/82; 423/308; 423/311; 433/201; 501/151
[58] Field of Search .................. 501/1, 95, 151; 3/1.9; 128/92 C; 433/201; 423/308, 311; 264/82, 60

[56] References Cited

U.S. PATENT DOCUMENTS 3,929,971 12/1975 Roy ...................................... 423/308
4,149,893 4/1979 Aoki et al. ............................ 106/35
4,222,128 9/1980 Tomonaga et al. ...................... 3/1.9
4,278,630 7/1981 Scheicher .............................. 264/60
4,321,042 3/1982 Scheicher ............................ 433/201

Primary Examiner—Helen M. McCarthy
Attorney, Agent, or Firm—Browdy and Neimark

[57] ABSTRACT

There are provided a novel sintered apatite body and a novel sintered apatite-mineral fiber material composite. The crystals of the sintered apatite have fine dense crystalline structures comprising needle-like fine crystals and are entangled together, whereby the mechanical properties of the sintered apatite body or composite are markedly enhanced. The sintered body and composite wherein the apatite is hydroxyapatite are useful for bioceramic uses. The sintered apatite body or composite is produced by baking an apatite material alone or in contact with a reinforcing mineral fiber material in the presence of water under pressure at a temperature lower than 1000° C., and further at a temperature lower than the temperature causing deterioration of the fiber material in the case of the composite.

25 Claims, 2 Drawing Figures

SINTERED APATITE BODIES AND COMPOSITES THEREOF

BACKGROUND OF THE INVENTION (1) Field of the Invention

This invention relates to a novel sintered apatite body comprising needle-like crystals and a novel sintered apatite-mineral fiber material composite. More particularly, this invention relates to a process for producing a novel sintered apatite body and a novel sintered composite consisting essentially of a matrix amount of an apatite and an effective amount of a reinforcing mineral fiber material, as well as the resulting sintered apatite-mineral fiber material composite. The process for sintering is characterized by baking an apatite material at a certain relatively-low temperature under pressure in the presence of water.

(2) Description of the Prior Art

The apatite materials for sintering are typically represented by hydroxyapatite, carbonate-apatite, fluoroapatite and chlororapatite. Hitherto have been proposed processes for sintering these apatites and especially hydroxyapatite at a high temperature of about 1100° C. or more. These sintered hydroxyapatite products, however, had a variety of serious problems such as poor mechanical strength properties (especially, impact strength and bending strength) due to their crystalline structures, large pores or flaws, and the like. For example, refer to R. W. RICE et al., J. Am. Ceram. Soc., 63 (3-4), (1980) 129–136, and T. KIJIMA et al., J. Am. Ceram. Soc., 62, (9-10) (1979) 455–460, the description being incorporated herein by reference. These conventional sintered apatite products have been expected to be useful for broad applications such as ceramic materials, electronic materials, filter materials, bioceramics (e.g., artificial bone and tooth implants) and the like, but it can not be said that they have been successfully utilized in these uses because of their insufficient mechanical properties, etc.

An attempt to reinforce the sintered apatite with reinforcing materials such as fibers would be considered naturally by those skilled in the art. This attempt, however, has been impeded by the following fundamental problems; (i) the conventional sintered apatite body baked at such a high temperature is rather brittle and weak in mechanical strength, and thus reinforcement with such fiber materials is not so effective, and (ii) most of such reinforcing materials are markedly deteriorated in mechanical strength under the conventional baking conditions as high as 1100° C. or more for sintering an apatite-reinforcing material composite.

In accordance with the conventional technical thoughts of producing a sintered apatite, it has been considered that the sintering of a pure apatite material containing no additive compound is substantially impossible at a temperature lower than 1100° or 1000° C. and especially lower than 800° C., or that even when the apatite could be narrowly sintered at such low temperatures the physical properties of the resulting sintered apatite are inevitably decreased to uselessness. In this connection, it has been unexpectedly found that apatite can be sintered under pressurization at a temperature lower than 1000° C. and preferably lower than about 800° C. in the presence of water to produce a sintered apatite body having far superior mechanical properties in comparison with the conventional sintered apatite.

The present invention produces a novel sintered apatite body having superior mechanical properties and uniform porosity. Studies were also made intensive researches on a sintered apatite-reinforcing fiber material composite to further enhance its mechanical properties. In the first course of the studies, glass fibers were used and iron fibers which are excellent as reinforcing materials and readily available at low costs, but the expected increase in mechanical properties was not observed with respect to the sintered apatite composites baked at about 700° C. It was then presumed that the problems were due to the deterioration of the fiber materials under oxidizing atmospheres even at about 700° C. and also due to the chemical affinity of the fiber materials with apatite at such a temperature. Thus, an attempt was made to produce apatite-fiber composites wherein glass fiber or carbon fiber was used as reinforcing materials at baking temperatures lower than 400° and 500° C., respectively, and has unexpectedly succeeded in the production of the apatite composites having excellent properties.

The reasons for the above-mentioned phenomena have not been fully clarified yet at present. It is considered, however, that the glass fiber or iron fiber has the physical and chemical affinity with apatite at a baking temperature of about 700° C. and thus the reinforcing fiber is deteriorated and also bonded to the sintered apatite firmly, whereby a sliding action between the fiber and sintered apatite is lost and the resulting composite is readily broken by the force applied thereto. On the contrary, the reinforcing fiber materials to be used in the present invention have sufficient physical affinity with apatite but are completely or substantially inert from the viewpoint of chemical affinity with apatite at the baking temperature of the present invention. Thus, it is considered that an apatite-reinforcing fiber composite having excellent mechanical properties and especially impact and bending strength properties can be unexpectedly obtained, because some sliding actions between the fiber material and sintered apatite are present in the composites according to the present invention. Incidentally, this may be rather surprising in view of the fact that, in conventional resin-fiber composites consisting of fiber materials and synthetic resins, the bonding affinity between the fibers and resins (for example by using a bonding accelerator) is desired and taken seriously, but the problems as raised above in the case of the sintered apatite-mineral fiber composites are irrelevant because the resin itself has some flexibility and the like in the case of the conventional resin composites instead of the above mentioned sliding actions.

It is an object of the invention to provide a process for producing a novel sintered apatite body and a novel sintered apatite-mineral fiber material composite.

It is another object of the invention to provide a novel sintered apatite body and a novel sintered apatite-fiber material omposite having broad ranges of applications by utilizing their excellent properties.

Other objects of the present invention will become apparent by the following description.

SUMMARY OF THE INVENTION

In accordance with the present invention, there is provided a process for producing a sintered apatite body, which comprises baking an apatite material selected from hydroxyapatite, carbonate-apatite, fluoroapatite, chloroapatite, precursor materials thereof, and mixtures thereof at a temperature lower than 1000° C. and preferably lower than about 800° C. under pressure in the presence of water to substantially sinter the apatite material. There is also provided a process for producing a sintered apatite-reinforcing mineral fiber material composite, which comprises baking under pressure a matrix amount of the apatite material and an effective amount of a reinforcing mineral fiber material in a substantially contacted state in the presence of water at a temperature defined above and lower than the temperature causing substantial deterioration of the fiber material and substantial bonding thereof to the apatite to substantially sinter the apatite material.

Thus, there are provided a novel sintered apatite body having fine dense polycrystalline structures wherein the crystals comprise or consist essentially of straight and/or curved needle-like crystals and are entangled together, which exhibits excellent physical properties, as well as a novel sintered apatite-mineral fiber material composite composed of the above mentioned sintered apatite matrix and a reinforcing mineral fiber material which is not substantially deteriorated and not substantially bonded to the sintered apatite. Incidentally, the features of the present invention will be exhibited if at least about 30% and generally 4% or more of the sintered crystals are composed of the needle-like crystals which are entangled together, although normally the crystals consist essentially of the needle-like crystals.

DETAILED DESCRIPTION OF THE INVENTION

Figure 1:
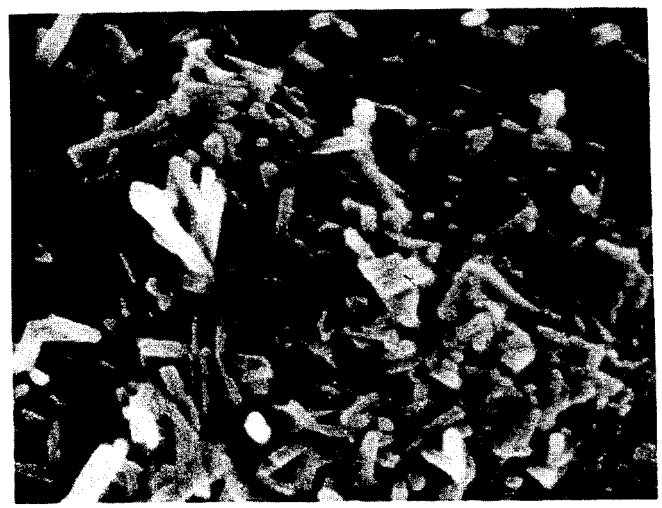
FIG. 1 is a scanning electrophotomicrograph (magnification ×30,000) of a sintered hydroxyapatite body according to the present invention, showing fine needle-like crystalline structures thereof.

The apatites to be used in the present invention include, for example, hydroxyapatite, carbonate-apatite, fluoroapatite, chloroapatite, mixtures thereof, and mixtures of subunit materials thereof which are converted to these apatites in the course of the baking step (herein referred to as an apatite precursor). Incidentally, apatite compounds are broadly defined by the following formula (I);

wherein, A=Ca, Pb, Mn, Na, K, etc.; X=P, As, V, Si, etc.; Z=OH, $CO_3$, F, Cl; and m is a number to satisfy the atomic valences. The apatite to be used in the present invention, however, is a more limited one.

The apatites to be used in the present invention are those compounds which have the fundamental structures represented by the following formula (II) and of which the atomic ratio of calcium to phosphorus (hereinafter referred to as Ca/P ratio) is within the range specified below;

wherein, Z is selected from OH, $CO_3$, F, Cl and mixtures thereof, and m is a number satisfying atomic valences substantially (e.g., 2 or 1). More specifically, in the formula (II) given above, the Ca/P ratio is not necessarily a stoichiometric ratio (5/3) but can be a non-stoichiometric ratio. In general, the Ca/P ratio is approximately in the range of 4/3 to 11/6 and preferably about 9/6 to about 5/3. As necessary, an inorganic non-phosphorus calcium compound such as calcium hydroxide can be intimately mixed with an apatite material having the Ca/P ratio of less than 5/3 to adjust its Ca/P ratio to about 5/3. In the case where a carbonate group-containing a calcium compound such as calcium carbonate is used therefor, a sintered apatite body or apatite-fiber composite containing $CO_3$ groups can be obtained by baking the materials at a temperature lower than the decomposition temperature of the carbonate compound. Incidentally, in the apatite represented by the formula (II), the Ca and/or P atom may be substituted by a small or impure amount of other atoms as illustrated in the definition of the formula (I).

The symbol Z in the formula (II) above can be one or two or more atoms or a group selected from OH, $CO_3$, F and Cl. In this case, the apatite is herein classified into hydroxyapatite, carbonate-apatite, fluoroapatite or chloroapatite, respectively, in accordance with the largest amount of OH, $CO_3$, F or Cl contained therein. All these apatites fall within the same hexagonal crystalline system, space group $C6_3/m$, and chemical formula number in unit lattice, and thus they have substantially the same sintering properties and similar physical properties. Incidentally, these apatites are available commercially and can be purified as necessary, or can be synthesized chemically by those skilled in the art.

From the viewpoint of uses and the like, the apatite to be used in the present invention is preferably hydroxyapatite represented by the formula (II) above wherein substantially all or a major amount (normally about 90% or more) of Z is OH group and the balance amount (normally about 10% or less) of Z is the other substituents. For bioceramic uses, the balance of Z if any is preferred to be $CO_3$ group.

By the term "a matrix amount" of apatite used with respect to the apatite-fiber material composite is meant the amount of the apatite material which can bind a reinforcing mineral fiber material (hereinafter sometimes referred to as fiber material) by the sintered apatite to form the sintered composite. The term "an effective amount" of the fiber material means the amount thereof which can reinforce the sintered composite and can be bound by the sintered apatite matrix to form the sintered composite.

Although the effective amount of the fiber material depends on the density and the like of the fiber material to be used, the ratio of the effective amount of fiber materials to the matrix amount of apatites is approximately by weight in the range of generally 0.5–70% to 99.5–30%, desirably 1–50% to 99–50%, preferably 2–40% to 98–60%, more preferably 5–30% to 95–70%, and typically 7–25% to 93–75%. Incidentally, the sintered composite of the present invention can of course contain optional materials such as fillers and coloring agents which are compatible with the apatite and fiber materials and are inert under the conditions of baking, machining and uses, so far as the properties of the resulting composite are not substantially deteriorated.

The mineral fiber materials to be used essentially as reinforcing materials encompass mineral (i.e. inorganic or metallic) fiber materials which have sufficient strength and will not be substantially deteriorated when they are baked in contact with the apatite material in the presence of moisture for at least 0.5 hour at a sintering temperature higher than about 150° C. and preferably about 170° C. (but lower than 1000° C. or 800° C.). The fiber materials preferred for use in the present invention include, for example, mullite fibers (800° C.), silicon carbide fibers (800° C.), carbon fibers (500° C.), apatite glass fibers (750° C.), glass fibers and preferably alkali-resistant glass fibers (500° C.), as well as silicon nitride fibers (1000° C.), silica fibers (1000° C.), alumina fibers (1000° C.), and the like, the temperatures shown in the parentheses being the approximate maximum values at which the fiber-containing apatite composite material can be baked according to the present invention without deteriorating the properties of the fiber material or the sintered apatite. Moreover, chemically inert metallic fiber materials such as metallic fibers coated thereon with an inorganic element or compound or substantially inert metallic fibers can also be used as the reinforcing fiber materials. The coated metallic fibers are generally preferred. For example, boron fibers wherein boron was vapor-deposited onto tungsten fibers can be advantageously used.

These reinforcing fiber materials are not restricted to the materials illustrated above and can be used alone or as optional mixtures thereof, as far as they exhibit satisfactory reinforcing effects and they are not deteriorated in the course of baking. As to the forms and dimensions of the reinforcing fiber materials, there can be applied technical knowledge of conventional glass fiber-synthetic resin composites. For example, they can be in the form of short fibers, long fibers, fiber yarns, fiber strands, wooly fibers, whiskers, nonwoven or woven fabrics, mixtures thereof, and the like. In the case of short fibers, the fiber length thereof is desired to be longer than the crystal length of the sintered apatite. The distribution of the mineral fiber material in the present sintered apatite composite can be in the state substantially orientated mono-, bi- or triaxially or in the state substantially unorientated and distributed irregularly. Also, the distribution of the fiber material can be uniformly dispersed in the sintered apatite matrix or dispersed dense (or rare or zero) toward the core of the composite and rare or zero (or dense) toward the surfaces of the composite. It is generally preferred that the fiber material is distributed dense toward the surface and is not exposed to the surface from the viewpoint of stress-resistant structural materials.

The sintered apatite body of the present invention can be produced by baking the above mentioned apatite material under pressure in the presence of a suitable amount of water at a temperature of about 150° C. to less than 1000° C. and preferably about 160° C. to about 800° C. When the sintering temperature is lower, the needle-like crystalline structures peculiar to the present sintered apatite tend to become finer and increase in mechanical strength. This tendency is markedly noted when the sintering temperature is normally about 700° C. and less, especially about 600° C. or less and typically about 500° C. or less, although the sintering is accelerated at a higher temperature. Thus, the lower sintering temperature is generally preferred in the present invention from the viewpoint of the enhanced mechanical properties of the resulting sintered body or composite. The amount of water to be co-existing with the apatite material in the baking step is, in addition to crystal water, an amount of non-crystal water (i.e. water except crystal water) in the range of 0.01% to about 25%, preferably about 0.05% to about 20%, more preferably about 0.1% to about 20% and typically about 3% to about 18% by weight of the apatite material used. When the amount of water is large, the sintering of the apatite tends to be accelerated. In the case where the water is more than about 25% and pressure is relatively low, the void of the resulting sintered apatite will generally become too large. Incidentally, when the apatite is baked in an open-heating means such as a hot press, the amount of water to be charged may be larger than 25%.

In the same fashion and conditions as described above, the mineral fiber-sintered apatite composite of the present invention can be produced by baking a matrix amount of the apatite material and an effective amount of the reinforcing mineral fiber material in a substantially contacted state at a temperature defined above and lower than the temperature causing substantial deterioration of the fiber material and substantial bonding thereof to the apatite material.

Although the sintering mechanism of the apatite in the present invention has not been fully clarified yet, it is considered that the apatite is dissolved and separated out at the baking temperature and then the separated apatite is recrystallized, entangled together and sintered. The dissolution and separation of apatite tend to be promoted under a higher pressure and/or in the presence of sufficient water. In this connection, in accordance with the present invention, the baking or sintering temperature can be considerably lowered under a higher pressure and in the presence of sufficient water in the baking step. Thus, the pressure to be employed in the sintering of the present invention is at least about 5 kgs/cm$^2$, preferably about 50 kgs/cm$^2$ or more, and typically about 500 kgs/cm$^2$ or more.

In the baking step of the present invention, there can be employed conventional techniques known to the sintering art. For example, there can be used a hot press method under a steam atmosphere, a closed heating method under pressure by means of an autoclave and the like, a closed high-frequency heating method under pressure, a hot isotactic pressing method, etc. The typical methods for the baking are summarized in the following. Incidentally, the time of baking is generally in the range of about 0.5 to about 30 hours.

(i) Hot press method

The material such as an apatite material, a mixture of an apatite material and a mineral fiber material, or a premolded article thereof is baked at a temperature defined above by means of a hot press under a pressure of about 5 kgs/cm$^2$ or more by applying thereto an atmosphere of steam or a steam-containing inert gas, preferably at a temperature of about 150° C. to about 500° C. under a pressure of about 10 to about 1000 kgs/cm$^2$. This method, however, is rather difficult to give a constant sintering condition.

(ii) Closed heating method under pressure

The material as mentioned above is baked in the presence of water at a temperature defined above by means of a pressure-proof vessel such as an autoclave under a pressure of five to several thousands atmospheres. When both the temperature and pressure are relatively low, a relatively longer time is needed for sintering the material. When the pressure is as high as 1000 kgs/cm$^2$ or more, the sintering can be advantageously conducted even at a temperature of 150° C. to about 200° C. Preferably, the material can be baked at a temperature of about 150° C. to about 500° C. under a pressure of about 20 to about 2000 kgs/cm².

(iii) Sintering in a sealed pressure-deformable capsule, etc.

In the closed heating method, closed high-frequency heating method, hot isotactic pressing method and the like described above, the material mentioned above can be sintered more effectively by baking the material which has been sealed in a pressure-deformable chemically-inert vessel (e.g., a capsule or a tube) together with water. The baking conditions are substantially the same as the above (ii), and preferably a pressure of about 40 to about 3000 kgs/cm² and a temperature of about 150° C. to about 500° C. By employing such a sealed vessel, the contents of the material and water can be maintained unchanged.

In the methods described above, the method (ii) is preferred and the method (iii) is most preferred. Incidentally, an apatite material or a mixture of an apatite material and a reinforcing fiber material can be molded into a desired shape by means of pressing or the like before the baking step; or the resulting sintered apatite body or composite can be machined into a desired shape.

The sintered apatite body obtained according to the present invention comprises or consists essentially of fine dense polycrystalline structures wherein the crystals are needle-like fine crystals and are entangled together, and the sintered apatite can be provided with suitable microporosity as necessary. The sintered apatite-fiber material composite is a composite wherein the fiber material is present in the unchanged state in contact with the sintered apatite matrix having the above mentioned crystalline structures, and the sintered composite can also be provided with suitable microporosity. In accordance with the sintering conditions of the present invention, the crystals of the present sintered apatite body or matrix have fine dense polycrystalline structures wherein the crystals comprise or consist essentially of straight and/or curved needle-like fine crystals and are entangled together, whereby the mechanical strength properties of the present sintered apatite body or apatite-fiber material composite are enhanced markedly. Incidentally, according to the conventional process for sintering the apatite at a temperature as high as 1100° C., the resulting sintered apatite is composed of relatively large hexagonal system crystals, and thus is markedly decreased in mechanical strength properties.

The strength properties of the sintered apatite body or composite is naturally decreased when the void volume or pore size of the sintered apatite body or matrix is too large. In order to obtain a sintered apatite body or composite having both the excellent strength and sufficient microporosity, it is desired that the sintering process is carried out under a relatively high pressure at a temperature as low as possible in the presence of moisture. Incidentally, the micropores obtained according to the present invention are normally in the form of open (continuous) pores.

The properties of the sintered apatite body and the sintered apatite-fiber material composite according to the present invention can have, for example, the following approximate values.

(a) Mean diameter of sintered apatite crystals: 0.01 to 5 $\mu m\phi$ (b) Mean length of sintered apatite crystals: 1 to 1000 $\mu m$ (c) Mean pore size of sintered apatite: 5 to 1000 $\mu m$ (d) Voids of sintered apatite: 0 to 40% by volume (e) Compression strength of sintered apatite: 300 to 1500 kg/cm²

(f) Bending strength of sintered apatite: 100 to 800 kg/cm²

(g) Impact strength of sintered apatite: 10 to 40 kg.cm/cm²

(h) Tensile strength of sintered apatite: 40 to 70 kg/cm²

(i) Compression strength of sintered composite: 350 to 2000 kg/cm²

(j) Bending strength of sintered composite: 1000 to 3500 kg/cm²

(k) Impact strength (charpy) of sintered composite: 50 to 200 kg.cm/cm²

(l) Tensile strength of sintered composite: 70 to 350 kg/cm²

Incidentally, some properties of the conventional sintered apatite body and composites, which were sintered at about 1100° C. by means of a hot press without a steam atmosphere applied thereto, are typically shown in Comparative Examples 1 through 3 below.

The sintered apatite body and apatite-fiber composite can be advantageously applied to the broad range of uses and especially to the fields where strength properties are required. Typically, the applications thereof are exemplified by ceramic materials which need strength properties, electronics materials, filter materials, chromatographic carriers, sensor elements (especially for physiological use), bioceramics (e.g., artificial bone, tooth and joint for the human or animal bodies), other uses where conventional fine ceramics are utilized, and the like. The above mentioned applications can be classified into industrial ceramic materials and bioceramic materials. The bioceramics require the compatibility with living organisms such as the human or animal bodies in addition to the strength properties and microporosity. Discussion will be made on the compatibility in the following.

It is known that the hard tissues (bone, tooth, etc.) of mammals and especially human bodies consist essentially of densified hydroxyapatite and more specifically consist of densified hydroxyapatite containing a small amount (several %) of $CO_3$ group. In this connection, there have been reported several studies on using sintered hydroxyapatite bodies for artificial bone and tooth implants. For example, refer to M. JARCO et al., J. Bioeng., 1, (1977) 79 and E. B. NERY et al., J. Periodontol, 46, (1975) 328, the description being incorporated herein by reference. Especially, porous sintered hydroxyapatite having a void of several percents or more has been appreciated to be practically satisfactory for compatibility with human tissues. The conventional sintered hydroxyapatite, however, is not used practically at the moment, which may be essentially due to nonuniform porosity and unsatisfactory mechanical properties such as impact strength and bending strength. On the other hand, the mineral fiber materials to be used in the present invention and especially the fiber materials of carbon, silicon carbide, mullite, silica, alumina, apatite glass and silicon nitride are known to have chemically and physiologically unirritating properties as well as excellent strength and elasticity. Moreover, it has been appreciated in the art that these fiber materials are practically satisfactory for compatibility with human tissues. These fiber materials are satisfactory for physiological compatibility especially when they are included as the composite in the sintered hydroxyapatite matrix. It is generally preferred that the surface of the present composite for bioceramic uses is substantially covered with the apatite matrix, that is, the fiber material is not substantially exposed.

The strength properties and open micropores having a void of about 3% to about 40% which have been required for such bioceramics are sufficiently provided by the sintered hydroxyapatite body and composite according to the present invention. Thus, the artificial hard tissue materials having suitable open pores, satisfactory strength properties and compatibility with the human and animal bodies can be obtained according to the present invention, wherein the above described conventional problems have been eliminated. In other words, because it has been confirmed in the art that conventional porous sintered hydroxyapatite bodies have compatibility with human tissues as shown in the above mentioned literature, the present sintered hydroxyapatite body and composite thereof improved in mechanical properties, suitable open pores, etc. can be used satisfactorily as such bioceramics.

Incidentally, the mode how the sintered hydroxyapatite body is successfully united with the human (or animal) tissues has not been fully elucidated. It is believed in the art, however, that, when a hydroxyapatite bioceramic material such as tooth or bone substitutes is implanted in the human tissues, the human body fluids such as blood contact with the bioceramic material and pass through the open micropores of the bioceramic material without rejection symptoms, and thus the hydroxyapatite components contained in the body fluids gradually deposit onto the micropores and surface of the hydroxyapatite bioceramic material to form natural deposition-densified hydroxyapatite layers, whereby the sintered hydroxyapatite body can be successfully unified with the human tissues by the aid of the natural densified hydroxyapatite layers. In the case of the present sintered hydroxyapatite-reinforcing mineral fiber material composite, the same mode of unification with the human tissues can be applied because the fiber material is substantially covered with or is contained in the sintered hydroxyapatite matrix and also the fiber material itself is compatible with the human tissues. In this connection, it is preferred that hydroxyapatite bioceramic materials have the Ca/P ratio in the vicinity of its theoretical value 5/3, e.g., in the range of about 9/6 to about 5/3.

The present invention will be further explained by way of the following examples. All the apatite materials to be used in the present invention have substantially the same chemical structures, crystalline systems, sintering properties and the like. Thus, those skilled in the art can readily produce substantially the same or similar sintered apatite bodies or composites of the present invention on the basis of the disclosure herein by using the materials and/or processes other than those shown in Examples. It should be construed that the invention is not restricted to the illustrative examples and the modifications and variations can be made within the spirit and scope of the invention.

In the following examples, the ratios and percentages are by weight unless otherwise specified.

EXAMPLE 1

Hydroxyapatite containing hydroxyl group and no other atom or group as the substituent (Ca/P ratio=95/60) was adjusted to a water content (except crystal water) of 5%. The hydroxyapatite powder was sealed in a pressure-deformable silver tube and then baked at 500° C. under a pressure of 1000 kgs/cm$^2$ for 3 hours by means of a pressure-proof vessel. The resulting sintered apatite body exhibited the following properties.

Compression strength: 520 kgs/cm$^2$
Bending strength: 710 kgs/cm$^2$
Tensile strength: 55 kgs/cm$^2$
Impact strength (Charpy): 16 kg.cm/cm$^2$
Void (open micropores): about 24% by volume The crystals of the sintered body are shown in FIG. 1 (magnification ×30,000) wherein fine needle-like crystals are entangled together.

EXAMPLE 2

A mixture of 85% hydroxyapatite powder used in Example 1 and 15% carbon fiber having a mean length of about 9 mm (thermal decomposition process grade) was adjusted to a water content of 5%. The mixture was then sealed in a pressure-deformable silver tube and baked at 400° C. for 7 hours as in Example 1. The resulting sintered apatite composite exhibited the following properties, the units of the strength properties being the same as in Example 1.

Compression strength: 780
Bending strength: 1850
Tensile strength: 200
Impact strength (Charpy): 115

Incidentally, it was observed in the bending test that on the rupture cross-section the carbon fibers were somewhat drawn out of the cross-section surface and ruptured. This will demonstrate that there exist some sliding actions between the fiber material and sintered apatite in the resulting composite.

EXAMPLE 3

The process of Example 2 was repeated except that 15% of mullite fiber having a mean length of about 9 mm was used instead of the carbon fiber. The resulting sintered apatite composite exhibited the following properties, the units of the strength properties being the same as in Example 1.

Compression strength: 690
Bending strength: 1720
Tensile strength: 185
Impact strength (Charpy): 110

Incidentally, it was also observed in the bending test that the mullite fibers were somewhat drawn out of the rupture cross-section and ruptured.

EXAMPLE 4

Calcium carbonate powder was incorporated into the hydroxyapatite powder (Ca/P ratio=95/60) to make the Ca/P ratio of the resulting mixture about 99/60. The mixed powder 85% was admixed with 15% of carbon fiber having a mean length of about 9 mm (thermal decomposition process grade). The resulting mixed material was adjusted to a water content of 5%, sealed in a pressure-deformable silver tube, and baked as in Example 2. The resulting sintered apatite composite exhibited the following properties, the units being the same as in Example 1. Incidentally, it is especially preferred from the viewpoint of the compatibility of the human tissues that the resulting composite contain a suitable amount of $CO_3$ group.

Compression strength: 820
Bending strength: 1870
Tensile strength: 195

EXAMPLE 5

The process of Example 4 was repeated except that the carbon fiber and calcium carbonate were replaced by 15% of silicon carbide fiber having a mean length of about 9 mm and by the corresponding amount of calcium hydroxide powder to make the Ca/P about 99/60, respectively. The resulting sintered apatite composite exhibited the following properties, the units being the same as in Example 1.

Compression strength: 835
Bending strength: 1910
Tensile strength: 190

COMPARATIVE EXAMPLE 1

Hydroxyapatite containing hydroxyl group and no other atom or group as the substituent (Ca/P ratio=95/60) was molded into a tablet about 5 mm×about 10 mm $\phi$ and then adjusted to a water content of 5%. The hydroxyapatite was compressed and baked at 1100° C. under 200 kgs/cm² for 2 hours by means of a hot press. The resulting sintered apatite body of the conventional type exhibited the following properties, the units being the same as in Example 1.

Compression strength: 320
Bending strength: 310
Tensile strength: 35
Impact strength (Charpy): 7

Figure 2:
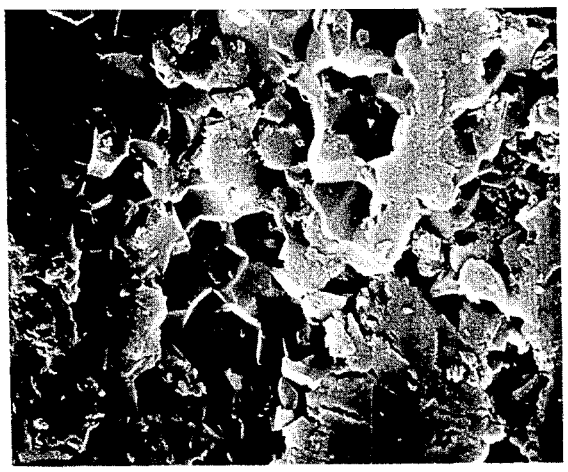
FIG. 2 is a scanning electrophotomicrograph (magnification ×7,500) of a sintered hydroxyapatite body according to a conventional sintering process at a high temperature, showing hexagonal-system crystalline structures thereof.

The crystals of the resulting sintered body are shown in FIG. 2 (magnification ×7,500), which are composed of hexagonal system crystalline structures.

COMPARATIVE EXAMPLE 2

A mixture of 85% hydroxyapatite powder used in Comp. Ex. 1 and 15% carbon fiber having a mean length of about 9 mm (thermal decomposition process grade) was molded into a tablet and then adjusted to a water content of 5%. The tablet was sintered as in Comp. Example 1 to show the following properties, the units being the same as in Example 1.

Compression strength: 310
Bending strength: 320
Tensile strength: 40
Impact strength (Charpy): 8

COMPARATIVE EXAMPLE 3

The process of the above Comp. Ex. 2 was repeated except that 15% of glass fiber having a mean length of about 9 mm was used. The resulting sintered apatite composite exhibited the following properties, the units being the same as in Example 1.

Compression strength: 305
Bending strength: 310
Tensile strength: 45
Impact strength: 8

Incidentally, in Comparative Examples 2 and 3, it was observed in the bending test that on the rupture cross-section the carbon fibers or glass fibers were ruptured on the cross-sectional surfaces. These facts will demonstrate that the fiber materials were deteriorated and also firmly bonded to the sintered apatite in the resulting composites. Also, it is to be noted that the hot press sintering steps in Comparative Examples 1 through 3 were conducted without applying thereto a steam atmosphere. This sintering step corresponds to the baking of hydroxyapatite in the absence of water, since substantially all the water present in the apatite is rapidly vaporized away from the mold of the hot press.

What is claimed is:

1. A process for producing a sintered apatite body, which comprises baking an apatite powder material selected from the group consisting of hydroxyapatite, carbonate apatite, fluoroapatite, chloroapatite, precursor materials thereof, the mixtures thereof, in the presence of co-existing water in an amount of not more than about 25% by weight of the apatite material in addition to crystal water, under pressure of at least about 5 kg/cm² at a temperature of not higher than about 800° C. to substantially sinter the apatite material, the crystals of the sintered apatite having fine dense crystalline structures comprising needle-like fine crystals entangled together.

2. The process according to claim 1, in which the apatite has the fundamental structure represented by the following formula and the atomic ratio of calcium to phosphorus in the apatite is in the range of about 4/3 to about 11/6;

$$Ca_{10}(PO_4)_6Z_m$$

wherein, Z is selected from OH, CO₃, F, Cl and mixtures thereof and m is a number satisfying atomic valences.

3. The process according to claim 1, in which the apatite material to be baked is sealed in a pressure-deformable vessel.

4. The process according to claim 2, in which a small amount of an inorganic non-phosphorus calcium compound is intimately mixed with an apatite material having the calcium/phosphorus ratio of less than 5/3 to adjust the Ca/P ratio of the apatite material to about 5/3.

5. The process according to claim 2, in which the apatite is hydroxyapatite wherein all or not less than about 90% of the substituent Z is OH group and the balance of Z if any is CO₃ group.

6. The process according to claim 5, in which the sintered apatite has open pore voids of about 3% to about 40% for bioceramic uses.

7. A process for producing a sintered apatite composite, which comprises baking a matrix amount of an apatite powder material selected from the group consisting of hydroxyapatite, carbonate apatite, fluoroapatite chloroapatite, precursor materials thereof, and mixtures thereof in contact with a reinforcing effective amount of reinforcing mineral fiber material under pressure of at least about 5 kg/cm², in the presence of coexisting water in an amount of not more than about 25% by weight of the apatite material in addition to crystal water, at a temperature not higher than about 800° C. to substantially sinter the apatite material and lower than the temperature causing substantial deterioration of the fiber material, the crystals of the sintered apatite having fine dense crystalline structures comprising needle-like fine crystals entangled together.

8. The process according to claim 7, in which the apatite has the fundamental structure represented by the following formula and the atomic ratio of calcium to phosphorus in the apatite is in the range of about 4/3 to about 11/6;

$$Ca_{10}(PO_4)_6Z_m$$

wherein, Z is selected from OH, CO₃, F, Cl and mixtures thereof and m is a number satisfying atomic valences.

9. The process according to claim 7, in which the material to be baked is sealed in a pressure-deformable vessel.

10. The process according to claim 8, in which a small amount of an inorganic non-phosphorus calcium compound is intimately mixed with an apatite material having the calcium/phosphorus ratio of less than 5/3 to adjust the Ca/P ratio of the apatite material to about 5/3.

11. The process according to claim 8, in which the apatite is hydroxyapatite wherein all or not less than about 90% of the substituent Z is OH group and the balance of Z if any is CO3 group.

12. The process according to claim 11, in which the sintered apatite has open pore voids of about 3% to about 40% for bioceramic uses.

13. The process according to claim 12, in which the fiber material is selected from carbon fiber, silicon carbide fiber, mullite fiber, silica fiber, alumina fiber, apatite glass fiber, silicon nitride fiber, and mixtures thereof for bioceramic uses.

14. A sintered apatite-mineral fiber material composite which consists essentially of an effective amount of a reinforcing mineral fiber material and a matrix amount of sintered apatite in contact with the fiber material, said apatite being selected from hydroxyapatite, carbonate apatite, fluoroapatite, chloroapatite and mixtures thereof, wherein the crystals of the sintered apatite have fine dense crystalline structures comprising at least about 30% of needle-like fine crystals and are entangled together and wherein the fiber material is not substantially deteriorated.

15. The composite according to claim 14, in which the apatite has the fundamental structure represented by the following formula and the atomic ratio of calcium to phosphorus in the apatite is in the range of about 4/3 to about 11/6;

$Ca_{10}(PO_4)_6Z_m$ wherein, Z is selected from OH, CO3, F, Cl and mixtures thereof and m is a number satisfying atomic valences.

16. The composite according to claim 14, in which the amount of the fiber material is in the range of about 1% to about 50% by weight and the amount of the apatite material is in the range of about 99% to about 50% by weight.

17. The composite according to claim 14, in which the fiber material is in the form of short fibers, long fibers, fiber yarns, fiber strands, wooly fibers, whiskers, nonwoven or woven fabrics, and/or mixtures thereof.

18. The composite according to claim 14, in which the fiber material is selected from carbon fiber, mullite fiber, silicon carbide fiber, apatite glass fiber, glass fiber, silicon nitride fiber, silica fiber, alumina fiber, chemically inert metallic fiber materials, and mixtures thereof.

19. The composite according to claim 15, in which the apatite is hydroxyapatite wherein all or not less than about 90% of the substituent Z is OH group and the balance of Z if any is CO3 group.

20. The composite according to claim 19, in which the sintered apatite has open pore voids of about 3% to about 40%.

21. The composite according to claim 20, in which the composite is biocompatible.

22. The composite according to claim 20, in which the fiber material is selected from carbon fiber, silicon carbide fiber, mullite fiber, silica fiber, alumina fiber, apatite glass fiber, silicon nitride fiber, and mixtures thereof.

23. The composite according to claim 22, in which the composite is biocompatible.

24. The composite according to claim 14, produced by baking an apatite powder material in contact with the fiber material under pressure of at least about 5 kg/cm².

25. The composite according to claim 24, in which the baking was conducted in the presence of co-existing water of not more than about 25% by weight of the apatite material in addition to crystal water and at a temperature of not higher than about 800° C.

* * * * *